(12) United States Patent
Shetty

(10) Patent No.: US 11,963,864 B2
(45) Date of Patent: Apr. 23, 2024

(54) METHOD AND SYSTEM FOR REDUCING PULMONARY FLOW

(71) Applicant: Varun Shetty, Bangalore (IN)

(72) Inventor: Varun Shetty, Bangalore (IN)

( * ) Notice: Subject to any disclaimer, the term of this patent is extended or adjusted under 35 U.S.C. 154(b) by 166 days.

(21) Appl. No.: 16/741,233

(22) Filed: Jan. 13, 2020

(65) Prior Publication Data
US 2020/0222172 A1    Jul. 16, 2020

(30) Foreign Application Priority Data
Jan. 11, 2019   (IN) .............................. 201941001363

(51) Int. Cl.
| | | |
|---|---|---|
| *A61F 2/06* | (2013.01) | |
| *A61F 2/82* | (2013.01) | |
| *A61F 2/958* | (2013.01) | |
| *A61L 31/04* | (2006.01) | |
| *A61F 2/95* | (2013.01) | |
| *A61L 31/02* | (2006.01) | |

(52) U.S. Cl.
CPC ................ *A61F 2/06* (2013.01); *A61F 2/958* (2013.01); *A61L 31/048* (2013.01); *A61F 2002/068* (2013.01); *A61F 2/9522* (2020.05); *A61F 2250/001* (2013.01); *A61L 31/022* (2013.01)

(58) Field of Classification Search
CPC .. A61F 2/24; A61F 2/2418; A61F 2/01; A61F 2/07; A61F 2/06; A61F 2/2403; A61F 2/2406; A61F 2/409; A61F 2/243; A61F 2/2433; A61F 2002/068; A61F 2/0063; A61F 2002/0068; A61F 2/0103; A61F 2/013; A61F 2/014; A61F 2002/018; A61F 2/82; A61B 17/0057; A61B 2017/00632; A61B 17/122; A61B 2017/00575; A61B 17/12036; A61B 17/12109; A61B 17/12172
See application file for complete search history.

(56) References Cited

U.S. PATENT DOCUMENTS

| | | | | |
|---|---|---|---|---|
| 3,844,302 | A * | 10/1974 | Klein | A45B 19/06 135/26 |
| 5,549,626 | A * | 8/1996 | Miller | A61F 2/01 606/198 |
| 5,683,411 | A * | 11/1997 | Kavteladze | A61B 17/12172 606/200 |
| 6,168,579 | B1 * | 1/2001 | Tsugita | A61B 17/12109 604/509 |
| 6,361,545 | B1 * | 3/2002 | Macoviak | A61B 17/221 606/151 |
| 6,652,556 | B1 * | 11/2003 | VanTassel | A61B 17/12159 606/200 |
| 6,949,113 | B2 * | 9/2005 | Van Tassel | A61B 17/12136 606/200 |
| 7,717,937 | B2 * | 5/2010 | Wahr | A61B 18/1492 606/213 |

(Continued)

*Primary Examiner* — Seema Mathew
(74) *Attorney, Agent, or Firm* — Kunzler Bean & Adamson

(57) ABSTRACT

A method and system discloses a medical device comprising a pre-crimped stent mounted on an inflatable means for inflating the pre-crimped stent. The pre-crimped stent mounted on an inflatable means further includes a membrane with a centrally positioned opening with a second expandable diameter, wherein the membrane covers one end of the pre-crimped stent, thereby reducing pulmonary flow in a pulmonary artery.

9 Claims, 3 Drawing Sheets

(56) References Cited

U.S. PATENT DOCUMENTS

| | | | | |
|---|---|---|---|---|
| 7,722,641 | B2* | 5/2010 | van der Burg | A61B 17/12136 606/142 |
| 2002/0062135 | A1* | 5/2002 | Mazzocchi | A61B 17/12109 606/200 |
| 2003/0069646 | A1* | 4/2003 | Stinson | A61F 2/2412 623/1.24 |
| 2004/0122467 | A1* | 6/2004 | VanTassel | A61B 17/12136 606/200 |
| 2010/0217385 | A1* | 8/2010 | Thompson | A61F 2/2412 623/2.36 |
| 2012/0289951 | A1* | 11/2012 | Kassab | A61B 18/02 606/21 |
| 2017/0215885 | A1* | 8/2017 | Goldie | A61B 17/12036 |

* cited by examiner

METHOD AND SYSTEM FOR REDUCING PULMONARY FLOW

FIELD OF INVENTION

The invention generally relates to a medical device for restricting blood flow in a vasculature. More specifically, the invention relates to providing a medical device system for protecting the pulmonary vasculature from pulmonary hypertension.

BACKGROUND OF INVENTION

Pulmonary Artery (PA) banding continues to be the most sought after palliative surgical technique for correcting one or more congenital heart diseases and associated conditions of hypertrophy and pulmonary hypertension. For instance, an arterial septal defect or a patent ductus arteriosus involves left-to-right shunting, thereby diverting blood to flow from the left upper chamber of the heart (left atrium) into the right upper chamber of the heart and further pumping it into the lungs, thereby leading to pulmonary over circulation. Accordingly, pulmonary artery banding is performed for addressing the arterial septal defect or patent ductus arteriosus.

Now, while pulmonary artery banding is performed for creating a narrowing/stenosing of the main pulmonary artery and reducing the pulmonary artery pressure, numerous procedural complications associated with the surgery leads to mortality in adults and children likewise. Especially, children and infants undergoing the corrective palliative surgery are unable to tolerate the complications associated with PA banding.

Therefore, there is a need in the art for identifying a non-invasive or minimally invasive procedure for addressing pulmonary hypertension/odema in adults and children.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the invention.

DETAILED DESCRIPTION

Before describing in detail embodiments that are in accordance with the invention, it should be observed that the embodiments reside primarily in combinations of components of a medical device for restricting pulmonary blood flow. Accordingly, the components have been described to include only those specific details that are pertinent to understanding the embodiments of the invention so as not to obscure the disclosure with details that will be readily apparent to those of ordinary skill in the art having the benefit of the description herein.

In this document, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element preceded by "comprises . . . a" does not, without more constraints, preclude the existence of additional identical elements in the process, method, article, or apparatus that comprises the element.

Further, before describing in detail embodiments that are in accordance with the invention, it should be observed that all the scientific and technical terms used in for describing the invention have same meanings as would be understood by a person skilled in the art.

Various embodiments of the invention provide a medical device for restricting pulmonary blood flow in one or more pulmonary arteries, thereby addressing pulmonary hypertension. More specifically, the medical device includes a pre-crimped stent mounted on an inflatable means for inflating the pre-crimped stent and a membrane with a centrally positioned opening, covering one end of the pre-crimped stent. One or more medical devices may be deployed in one or more vasculatures.

Figure 1:
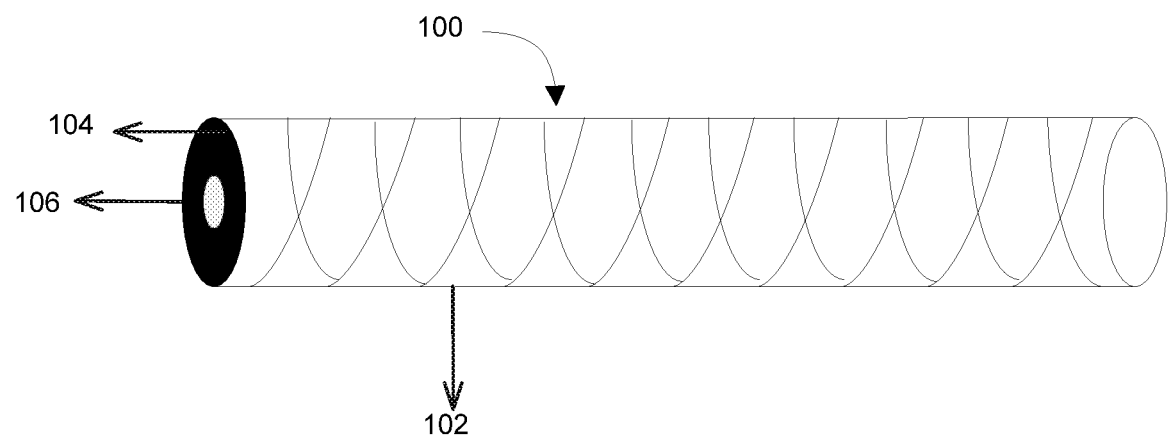
FIG. 1 is illustrative of a medical device for restricting pulmonary blood flow in accordance with an embodiment of the invention.

FIG. 1 illustrates a medical device 100 for restricting pulmonary blood flow in accordance with an embodiment of the invention. Medical device 100 further includes a pre-crimped stent 102 which is mounted on an inflatable means for inflating pre-crimped stent 102. Medical device 100 includes a membrane 104 covering one end of pre-crimped stent 102. In a preferred embodiment, membrane 104 is at a distal end of pre-crimped stent 102. Membrane 104 further includes a centrally positioned opening 106.

Figure 2:
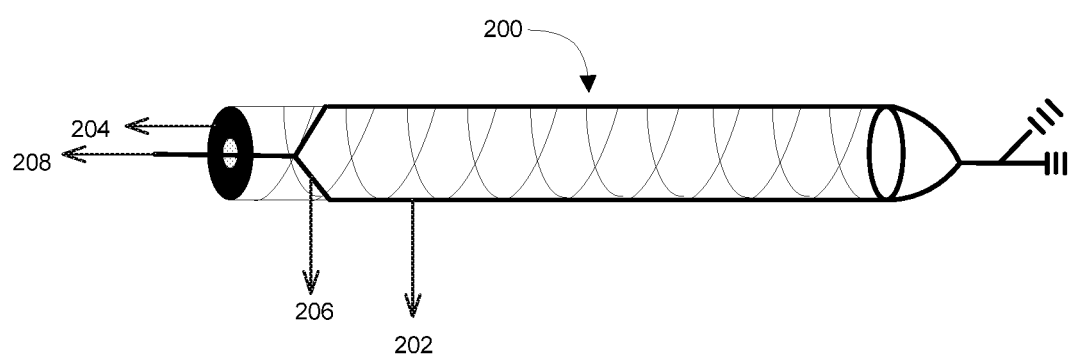
FIG. 2 is illustrative of a medical device in an uninflated state for restricting pulmonary blood flow in accordance with an exemplary embodiment of the invention.

FIG. 2 is illustrative of a medical device 200 in an uninflated state. As illustrated in FIG. 2, medical device 200, includes a pre-crimped stent 202 at a first expandable diameter mounted on a balloon 206 in an uninflated state. Medical device 200 further includes a membrane 204, positioned at a distal end of the pre-crimped stent 202 mounted on balloon 206. Membrane 204 includes a centrally positioned opening 208 with a second expandable diameter. In a preferred embodiment, diameter of centrally positioned opening 208 is $\frac{1}{3}^{rd}$ of a diameter of membrane 204. Diameter of centrally positioned opening 208 can be expanded further by balloon dilatation if required.

Figure 3:
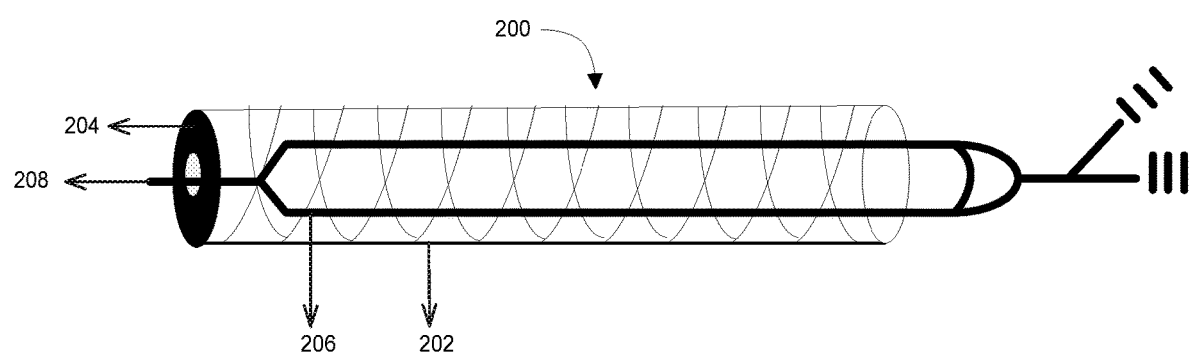
FIG. 3 is illustrative of a medical device in an inflated state, the medical device includes a balloon as an inflatable means and a membrane with a centrally positioned opening in accordance with an exemplary embodiment of the invention.

FIG. 3 is illustrative of medical device 200 in an inflated state. As illustrated in FIG. 3, pre-crimped stent 202 mounted on the inflatable means, balloon 206, includes pre-crimped stent 202 at a first expandable diameter mounted on balloon 206 in an inflated state. Medical device 200 further includes membrane 204, positioned at a distal end of the pre-crimped stent 202 mounted on balloon 206. Membrane 204 includes centrally positioned opening 208 with a second expandable diameter. In an inflated state, the second expandable diameter of centrally positioned opening 208 is proportionate to the first expandable diameter of pre-crimped stent 202. In a preferred embodiment, the second expandable diameter is about $\frac{1}{3}^{rd}$ of the first expandable diameter.

In an implementation, medical device 200 is employed in one or more pulmonary arteries for restricting pulmonary blood flow. Medical device 200 includes pre-crimped stent 202 and balloon 206 in an uninflated state during deployment in a pulmonary artery. Medical device 200 further includes membrane 204 that covers one end of the pre-crimped stent. For deploying the pre-crimped stent in a pulmonary artery via catherization techniques, a balloon tipped catheter/balloon is placed over a guide wire, via a femoral vein. Accordingly, pre-crimped stent 202 mounted on balloon 206 deployed in the one or more pulmonary arteries is operably configured to establish contact with one or more walls of the one or more branched pulmonary arteries. Pre-crimped stent 202 assumes a first expandable diameter in accordance with a circumferential diameter of the pulmonary artery, in response to an inflated state of the balloon. Verification of an optimal pre-crimped stent's first expandable diameter is based on a body weight of a user of the medical device.

Consider an exemplary scenario, wherein medical device 200 is introduced into a target pulmonary artery via a 5 Fr catheter via a femoral vein of a user under fluoroscopy. On deployment within the target pulmonary artery, further confirmation is performed by an angiogram. In a preferred embodiment, an optimal position for a medical device in a target pulmonary artery is at a pre-branching junction of one or more pulmonary arteries without obstructing segmental branches. During deployment, a pre-crimped stent in an inflated state cannot be re-captured, therefore optimum positioning of the pre-crimped stent within a target pulmonary artery is crucial prior to deployment.

Furthermore, any potential leaks between pre-crimped stent 202 and the one or more walls are resolved by additional balloon dilatation. Multiple angiograms are performed for confirmation on prevention of obstruction in segmental branching.

In another implementation, the medical device for restricting pulmonary blood flow in one or more pulmonary arteries includes a self-expanding pre-crimped stent. On deploying the self-expanding pre-crimped stent in one or more pulmonary arteries, the self-expanding pre-crimped stent expands cylindrically towards one or more portions of the one or more pulmonary artery walls for secure attachment. The self-expanding stent includes a membrane with a centrally positioned opening with an expandable diameter for facilitating restrictive flow of blood.

In an exemplary embodiment, pre-crimped stent 202 is made of a combination of nickel and cadmium. Further, on deployment of pre-crimped stent 202 mounted on balloon 206 within a pulmonary artery in an uninflated state, balloon 206 is inflated in an ensuing step, wherein the first expandable diameter of pre-crimped stent 202 is in accordance with a diameter of the one or more pulmonary arteries. Membrane 204 is usually made of a polyester fiber material, more specifically polytetrafluoroethylene.

In another embodiment, self-expanding pre-crimped stent is made of a combination of nickel and cadmium. The membrane with a centrally positioned opening is made of a polyester fiber material, more specifically polytetrafluoroethylene.

Centrally positioned opening 208 in membrane 204 of medical device 200 in an inflated state constitutes by far the only opening for enabling flow of blood within a pulmonary artery. In an embodiment the second expandable diameter is adjusted in accordance with a pressure drop across with pre-crimped stent by virtue of an inflatable balloon. The pressure drop before and after the deployment of pre-crimped stent 202 are measured by an end hole catheter to ensure adequate reduction in pulmonary artery pressure. Again, antegrade flow across pre-crimped stent 202 mounted on balloon 206 is a mandatory requirement for hemodynamic stability and therefore the second expandable diameter is accordingly adjusted.

According to one aspect of the medical device, pre-crimped stent 202 mounted on balloon 206 is adapted to secure medical device 200 to the one or more walls of the pulmonary artery and membrane 204 with centrally positioned opening 208 facilitating restricted flow of pulmonary blood from one side of medical device 200 to the other side of medical device 200 through medical device 200. Therefore, membrane 204 is structurally ring shaped to enable channelizing restrictive flow of the pulmonary blood through a given pulmonary artery.

The method and system advantageously enables effective postponing of a palliative corrective surgery from being an immediate solution to correcting of pulmonary defects and thereby reducing the excessive pulmonary blood flow (into the lung) and protect the pulmonary vasculature from hypertrophy and pulmonary hypertension.

Those skilled in the art will realize that the above-recognized advantages and other advantages described herein are merely exemplary and are not meant to be a complete rendering of all the advantages of the various embodiments of the invention.

In the foregoing complete specification, specific embodiments of the invention have been described. However, one of ordinary skill in the art appreciates that various modifications and changes can be made to the invention without deviating from the scope of the invention. Accordingly, the complete specification is to be regarded in an illustrative rather than a restrictive sense, and all such modifications are intended to be included within the scope of the invention.

I claim:

1. A medical device for restricting pulmonary blood flow in one or more pulmonary arteries, the medical device comprising:
   a pre-crimped stent comprising a cylindrical configuration having a length and a first continuous expandable diameter, wherein the pre-crimped stent is configured to expand cylindrically upon deployment to contact at least one wall of a pulmonary artery, wherein the length is mounted on an inflatable means configured to automatically inflate from an uninflated state to an inflated state in response to a pressure drop across the length, wherein the first continuous expandable diameter is configured to expand in response to the inflatable means moving from the uninflated state to the inflated state; and
   an impermeable disk-shaped membrane configured to cover one end of the pre-crimped stent, the impermeable disk-shaped membrane comprising a centrally positioned opening having a second continuous expandable diameter configured to automatically expand in proportion to the first continuous expandable diameter, wherein the second continuous expandable diameter is also disposed at the one end.

2. The medical device of claim 1, wherein the inflatable means comprises a balloon.

3. The medical device of claim 1, wherein the pre-crimped stent comprises nickel and cadmium.

4. The medical device of claim 1, wherein the inflatable means is configured to inflate upon deployment within the pulmonary artery such that the first continuous expandable diameter substantially corresponds to a diameter of the pulmonary artery.

5. The medical device of claim 1, wherein the impermeable disk-shaped membrane comprises a polyester fiber material.

6. The medical device of claim 5, wherein the polyester fiber comprises polytetrafluoroethylene.

7. The medical device of claim 1, wherein the pre-crimped stent is configured to be surgically extricated from the pulmonary artery after deployment.

8. The medical device of claim 1, wherein the pre-crimped stent is configured to be deployed into the pulmonary artery by a catheter.

9. The medical device of claim 1, wherein the pre-crimped stent is configured to be a self-expanding upon deployment within the pulmonary artery.

* * * * *